United States Patent
Abdel-Rahman et al.

(10) Patent No.: US 6,781,384 B2
(45) Date of Patent: Aug. 24, 2004

(54) ENHANCING THE STABILITY OF ELECTRICAL DISCHARGES

(75) Inventors: Mahmoud Abdel-Rahman, Newark, DE (US); Robert P. Rhodes, Lincoln University, PA (US)

(73) Assignee: Agilent Technologies, Inc., Palo Alto, CA (US)

( * ) Notice: Subject to any disclaimer, the term of this patent is extended or adjusted under 35 U.S.C. 154(b) by 45 days.

(21) Appl. No.: 09/910,731

(22) Filed: Jul. 24, 2001

(65) Prior Publication Data

US 2003/0020481 A1 Jan. 30, 2003

(51) Int. Cl.[7] .............................................. G01N 27/62
(52) U.S. Cl. ...................... 324/464; 73/23.22; 73/35.08
(58) Field of Search ........................ 324/464; 340/579; 73/23.22, 22.25, 35.08, 116; 315/11

(56) References Cited

U.S. PATENT DOCUMENTS

| | | | |
|---|---|---|---|
| 3,742,475 A | | 6/1973 | Liebermann et al. |
| 3,781,838 A | * | 12/1973 | Primmer ..................... 315/11 |
| 4,090,308 A | * | 5/1978 | Stuck ......................... 324/464 |
| 4,446,560 A | | 5/1984 | Gabor |
| 4,629,992 A | * | 12/1986 | Nudelmont ................. 324/464 |
| 4,698,586 A | | 10/1987 | Roos et al. |
| 4,975,648 A | | 12/1990 | Lawson et al. ............. 324/464 |
| 5,153,519 A | | 10/1992 | Wentworth et al. ........ 324/464 |
| 5,914,604 A | * | 6/1999 | Bahr ......................... 73/35.08 |
| 6,029,627 A | * | 2/2000 | Van Dyne .................... 73/116 |
| 6,037,179 A | | 3/2000 | Abdel-Rahman ............ 436/52 |

FOREIGN PATENT DOCUMENTS

| | | |
|---|---|---|
| DE | 0152883 | 12/1981 |
| JP | 600114746 | 6/1985 |
| JP | 600114747 | 6/1985 |
| WO | WO01/20645 | 3/2001 |
| WO | WO 01/20645 | 3/2001 |

* cited by examiner

*Primary Examiner*—N. Le
*Assistant Examiner*—Timothy J. Dole

(57) ABSTRACT

An electronic circuit and a method of generating an electrical discharge for an ionization detector system. The electronic circuit includes a transformer with a primary portion and a secondary portion. The circuit and method produce an electrical discharge across a set of electrodes. The discharge is stable over time and has relatively low peak currents associated therewith.

20 Claims, 6 Drawing Sheets

RELATED
ART**

ENHANCING THE STABILITY OF ELECTRICAL DISCHARGES

BACKGROUND OF THE INVENTION

1. Field of the Invention

The present invention relates generally to devices that may be used to generate and control electrical discharges in ionization sources of analytical devices.

2. Description of the Related Art

Gas chromatography devices can separate a gas mixture into the mixture's component gases and, after the separation, can quantify each component gas. A detector 10 used for analyzing a component gas is illustrated in FIG. 1A. The type of detector 10 illustrated in FIG. 1A is a discharge ionization detector that has previously been disclosed in U.S. Pat. No. 4,975,648 to Lawson et. al., the contents of which are incorporated herein by reference.

The detector 10 illustrated in FIG. 1A includes a housing 20 that has, formed within it, a discharge chamber 30, and ionization chamber 40, and an aperture 50 that connects the discharge chamber 30 and the ionization chamber 40. Also formed within the housing 20 are a surrounding gas inlet 60 that leads to the discharge chamber 30, a sample inlet 70 that leads to the ionization chamber 40 and a sample outlet 80 that also leads to the ionization chamber 40.

Within the discharge chamber 30 are a pair of spark-generating electrodes 90. One of the spark electrodes 90 has a small ball at the end thereof, while the other spark electrode 90 has a sharpened tip. Each of the spark electrodes 90 is connected to a separate pin 100 that supports the electrode 90 attached to it at a spatial location within the discharge chamber 30.

Each of the pins 100 is contained within a separate sheath 110 that protrudes from both sides of a sealing flange 120. The sealing flange 120 can be screwed into or otherwise fixed to one end of the housing 20.

Outside of the housing 20 and wrapped around each sheath 110 is a separate insulating plug 130. Each plug 130 leads to a separate wire 140 and each of the wires 140 is electrically connected to the same electronic circuit 150.

The electronic circuit 150 provides electrical current to each of the spark electrodes 90 during operation of the detector 10. The timing, duration and intensity of the sparks created between the electrodes 90 is controlled by the electronic circuit 150.

A collector electrode 160 and an emitter electrode 170 are position within the ionization chamber 40 of the detector 10 and are held in place via a bottom flange 180 that is fitted into the housing 20. A pair of wires 190 connect to the collector electrode 160 and the emitter electrode 170, respectively, and lead to a pair of electrical couplings 200. The wires 190 provide current to the collector electrode 160 and emitter electrode 170 when the detector 10 is in operation.

During operation, a surrounding or carrier gas, such as helium, is allowed to flow into the discharge chamber 30 through the surrounding gas inlet 60. The spark electrodes 90 are then provided with current from the electronic circuit 150 and are placed in close enough proximity to generate an electrical arc or spark across the electrodes 90. The electrical spark causes the surrounding gas to discharge photons and metastables at a characteristic energy level.

The photons and metastables then travel through the aperture 50 of the housing 20 and into the ionization chamber 40 that is filled with a gas that has been separated by the gas chromatography apparatus and that has been flowing into the ionization chamber 40 through the sample inlet 70. The photons and metastables then mix with and interact with the separated sample gas, cause electrons to be generated in the ionization chamber 40, cause a current to form between the collector electrode 160 and the emitter electrode 170, and allow for the concentration of the separated gas to be determined.

In order for the detector 10 to operate properly, the electrical discharges between the spark electrodes 90 are preferably chosen to be very stable. Instability in the discharges can cause serious deterioration of the analytical measurements being performed in the detector 10. Such deteriorations can include shifts or oscillations in the analytical measurement. Hence, the detector 10 shown in FIG. 1A is generally attached to an electronic circuit 150 that attempts to drive the discharge while enhancing the stability of the discharge.

FIG. 1B illustrates an electronic circuit 150 according to the related art that contains a resistor R, a first electrode 240, a second electrode 250, and a high voltage direct current (DC) power source 400. However, the DC discharges driven by the circuit 150 illustrated in FIG. 1B are unstable due to uncontrolled wandering of the space charge present in the discharge area over time.

In order to enhance the stability of the discharges compared to the circuit 150 illustrated in FIG. 1B, related art circuits 150 such as the one illustrated in FIG. 1C have been employed and have been disclosed in U.S. Pat. No. 5,153,519 to Wentworth et. al., the contents of which are incorporated herein by reference. The circuit 150 illustrated in FIG. 1C includes a resistor R, a first electrode 240 and a second electrode 250. According to such related art circuits 150, short, periodic, DC pulses 410 are used to produce discharges across the spark electrodes 90. However, the DC pulses generated by the circuit 150 illustrated in FIG. 1C results in discharge peak currents that are far greater than the average current.

Larger peak currents can cause deterioration and damage of the surface of the cathode spark electrode 90, particularly when noble gases with larger atomic masses are employed as the surrounding gas. Hence, the high peak currents generated by the circuit 150 illustrated in FIG. 1C require large cathode areas and large cross-sectional discharge areas.

Such large-area configurations are disfavored because they do not enable high the gas atoms to achieve high linear velocities between the discharge chamber 30 and the ionization chamber 40. Low linear velocities allow sample gas at high concentrations to diffuse into the discharge chamber 30 and quench the discharge. Hence, the detector's 10 sample dynamic range is not optimized, as further discussed in U.S. Pat. No. 6,037,179 to Abdel-Rahman, the contents of which are incorporated herein by reference.

To summarize, the electronic circuit 150 illustrated in FIG. 1B and discussed above leads to instabilities in the DC discharges observed between the spark electrodes 90. On the other hand, the electronic circuit 150 illustrated in FIG. 1C requires high peak currents to effectuate ionization, can cause damage to the electrodes 90, and requires a large discharge cross-sectional area.

BRIEF SUMMARY OF THE INVENTION

According to one embodiment, an electronic circuit that includes a first electrode for electrical connection to an ionization detector system, a second electrode for electrical connection to an ionization detector system, and a transformer electrically connected to the first electrode and to the second electrode for creating a spark between the first electrode and the second electrode.

According to another embodiment, a method of generating an electrical discharge for an ionization detector system that includes providing a first electrode and a second electrode, each electrically connected to an ionization system, providing a transformer electrically connected to the first electrode and the second electrode, inputting a DC voltage into the primary portion of the transformer, and generating a discharge current between the first electrode and the second electrode.

BRIEF DESCRIPTION OF THE DRAWINGS

The invention will be described by way of example, in the description of exemplary embodiments, with particular reference to the accompanying drawings in which.

DETAILED DESCRIPTION OF THE INVENTION

Figure 2A:
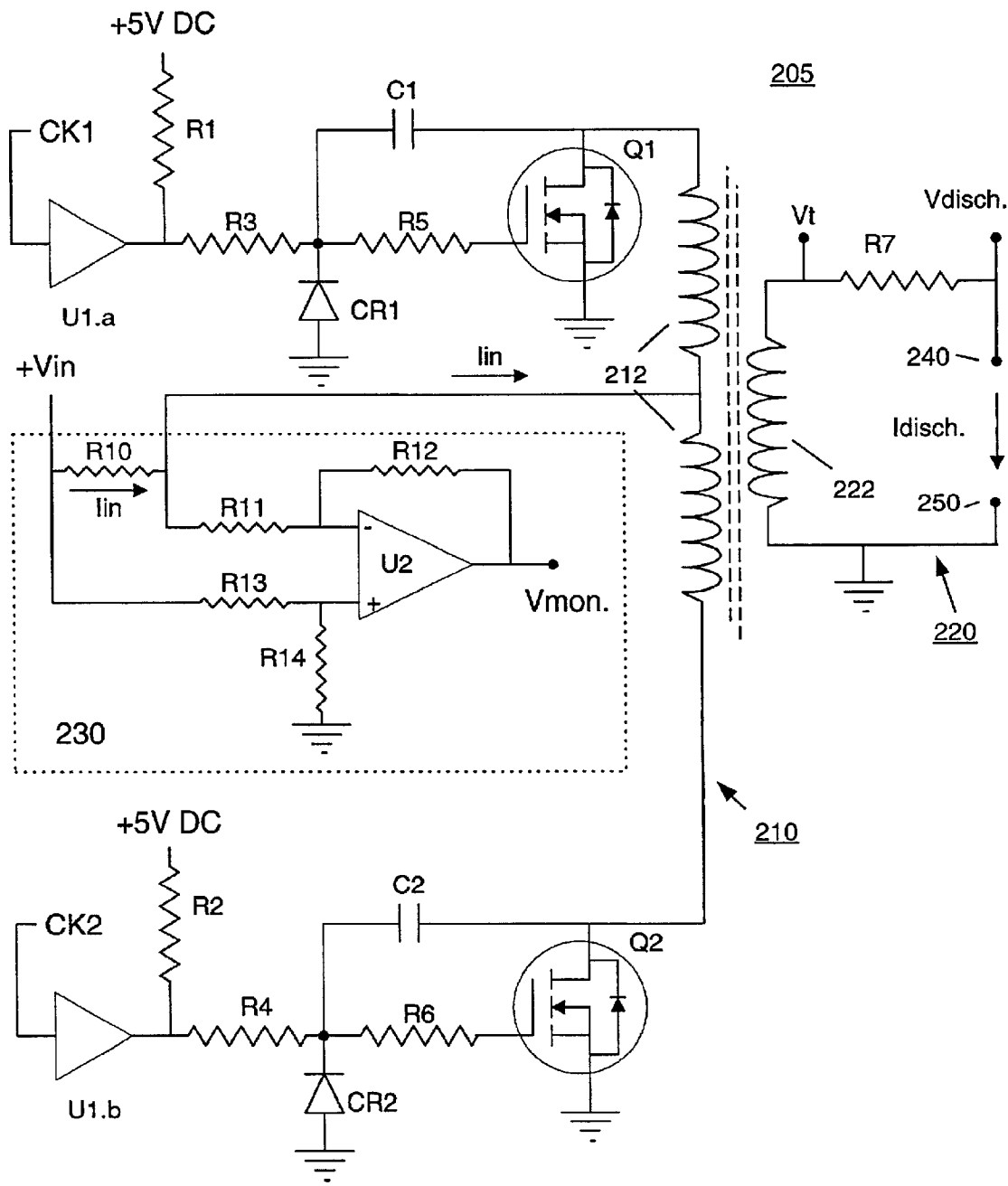
FIG. 2A illustrates an embodiment of an electronic circuit according to the present invention, using a transformer and a resistor electrically connected to the secondary portion of the transformer.

FIG. 2A illustrates an electronic circuit 150 according to a first embodiment of the present invention wherein an alternating current (AC) source is used to generate a current across the spark electrodes 90. According to certain embodiments, the AC source can also include a DC component.

The electronic circuit 150 illustrated in FIG. 2A includes a step-up transformer 205 with a primary portion 210 that includes a primary coil 212 and a secondary portion 220 that includes a secondary coil 222. Each coil 212, 222 in FIG. 2A contains a different number of loops, with the primary coil 212 containing more loops than the secondary loop 222. However, the configuration of FIG. 2A is not limiting of the present application and coils 212, 222 with numbers and ratios of loops different from what is illustrated are also within the scope of the present invention.

The primary portion 210 includes two TTL conjugated clock inputs CK1, CK2, that each lead to one of the open collector buffers U1.a, U1.b, in the circuit 150 and to a set of electronic devices including a set of resistors R1, R2, R3, R4, R5, R6, switching diodes, CR1, CR2, 5V DC external voltages, feedback capacitors, C1, C2, and power field effect transistors (FET) with built-in diodes Q1, Q2.

Resistor R10 is a sense resistor sufficiently small enough to prevent significant voltage drop across it. However, resistors R11 and R13 have larger resistance values than resistor R10 and draw very little current from the power supply. When the resistance values are chosen such that R11/R12=R13/R14, which is usually the case, the output voltage of the monitor $V_{mon}=(R12/R11)*R*I_{in}$. In other words, the monitored voltage $V_{mon}$ is directly proportional to the input current $I_{in}$.

The two TTL conjugated clocks CK1, CK2, can have frequencies that can be chosen to be on the order of between 1 kHz or less to 16 kHz or more. The feedback capacitors C1, C2, and associated electronic components dampen the fly-back action of the transformer 205 and also protect against the virtual short circuit should the power FETs Q1, Q2, ever conduct at the same time to produce opposing and canceling fluxes in the transformer 205.

Also included in the primary portion 210 of the transformer 205 is a lead to an input voltage $V_{in}$ that produces current $I_{in}$ across a resistor R10. This input voltage $V_{in}$ is typically chosen to be a regulated DC voltage. The lead from the input voltage $V_{in}$ can be electrically connected to a series of resistors R10, R11, R12, R13, R14, and an operational amplifier U2, contained in a current monitor section 230 of the circuit 150 wherein the input current $I_{in}$ can be monitored as $V_{mon}$. The input voltage $V_{in}$ then can assist in powering the secondary portion 220 of the transformer 205.

The secondary portion 220 of the transformer 205 illustrated in FIG. 2A includes a ground, a single resistor R7, and two probes $V_t$, $V_{disch}$, located on either side of the resistor R7. The secondary portion 220 of the transformer 205 also contains a first electrode 240 and a second electrode 250 across which an electrical arc or spark may be formed when the circuit is in operation.

Figure 2B:
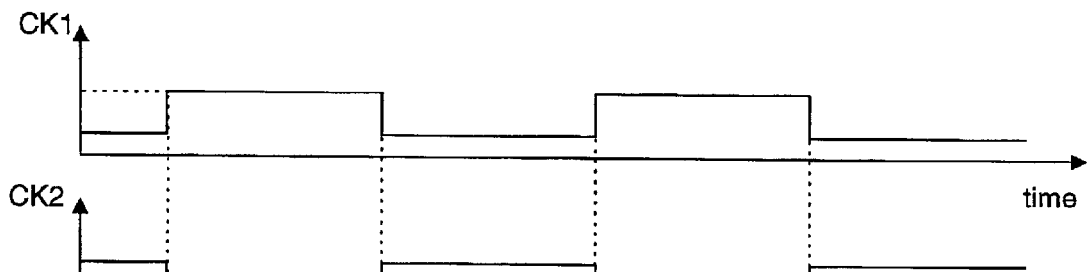
FIGS. 2B–2E illustrate the waveforms of various signals monitored within the electronic circuit illustrated in FIG. 2A.

FIGS. 2B–2E illustrate several graphs of signals monitored as a function of time in the electronic circuit 150 illustrated in FIG. 2A. FIG. 2B illustrates wave forms that represent the voltage levels of the conjugated clocks CK1, CK2, as a function of time and shows that the clocks CK1, CK2, are cycled between "on" and "off" values at regular intervals such that one clock CK1, CK2, is always in the "on" position.

Figure 2C:
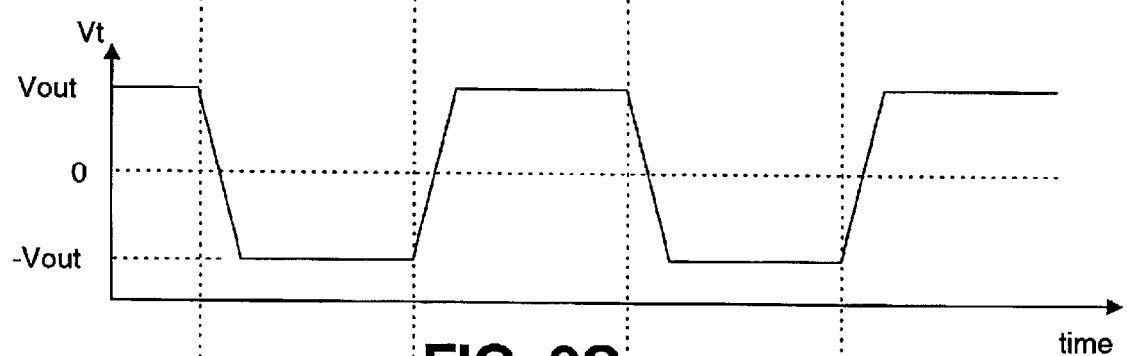

FIG. 2C illustrates the voltages monitored at position $V_t$ within the secondary portion 220 of the transformer 205. This graph shows a maximum voltage $V_{out}$, a minimum voltage $-V_{out}$, and also shows that a time lag exists as the voltage switches between these extreme values.

Figure 2D:
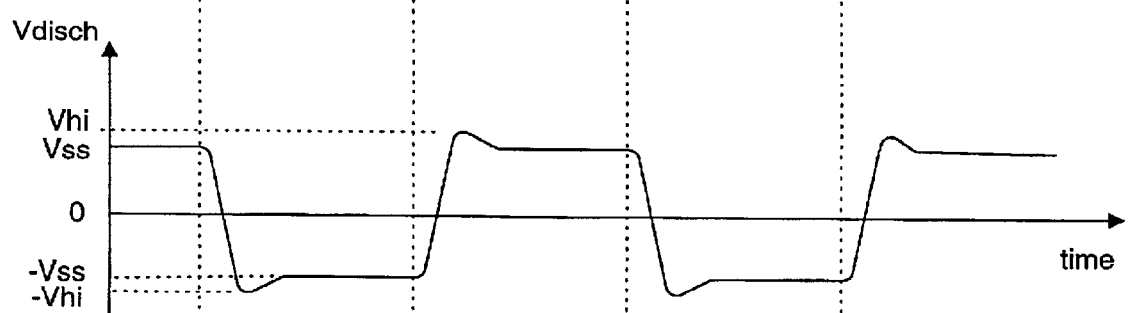

FIG. 2D illustrates the discharge voltage $V_{disch}$ as the circuit 150 operates. The maximum discharge voltage $V_{disch}$ peaks at $V_{hi}$ after each occurrence of a circuit switch. $V_{disch}$ then attains a steady state plateau $V_{ss}$ that can be on the order of between 200 and 300 volts. The small difference between $V_{hi}$ and $V_{ss}$ in the circuit illustrated in FIG. 2A can be attributed to the fact that some of the sample gas in the ionization chamber 40 remains ionized as $V_{disch}$ switches polarity.

Figure 2E:
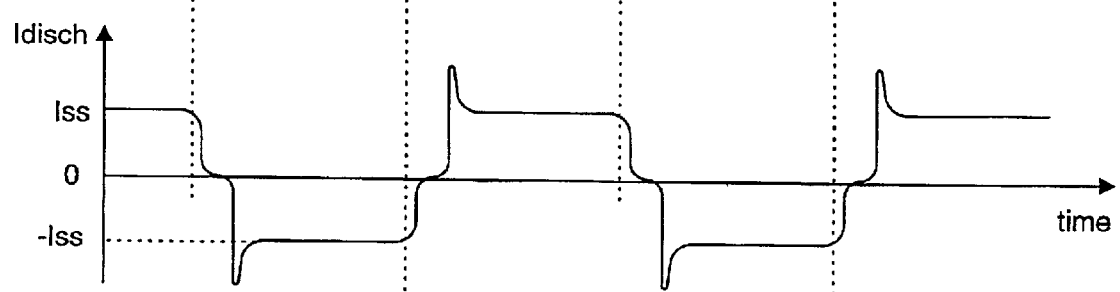

FIG. 2E illustrates the discharge current $I_{disch}$ that flows between the first electrode 240 and the second electrode 250 illustrated in FIG. 2A when the circuit 150 is in operation. Two steady state plateaus of current are illustrated, one at a value of $I_{ss}$ and the other at a value of $-I_{ss}$. The steady state plateau of the discharge current $I_{disch}$ is set by the formula: $I_{ss}=(V_{out}-V_{ss})/R7$.

Figure 1A:
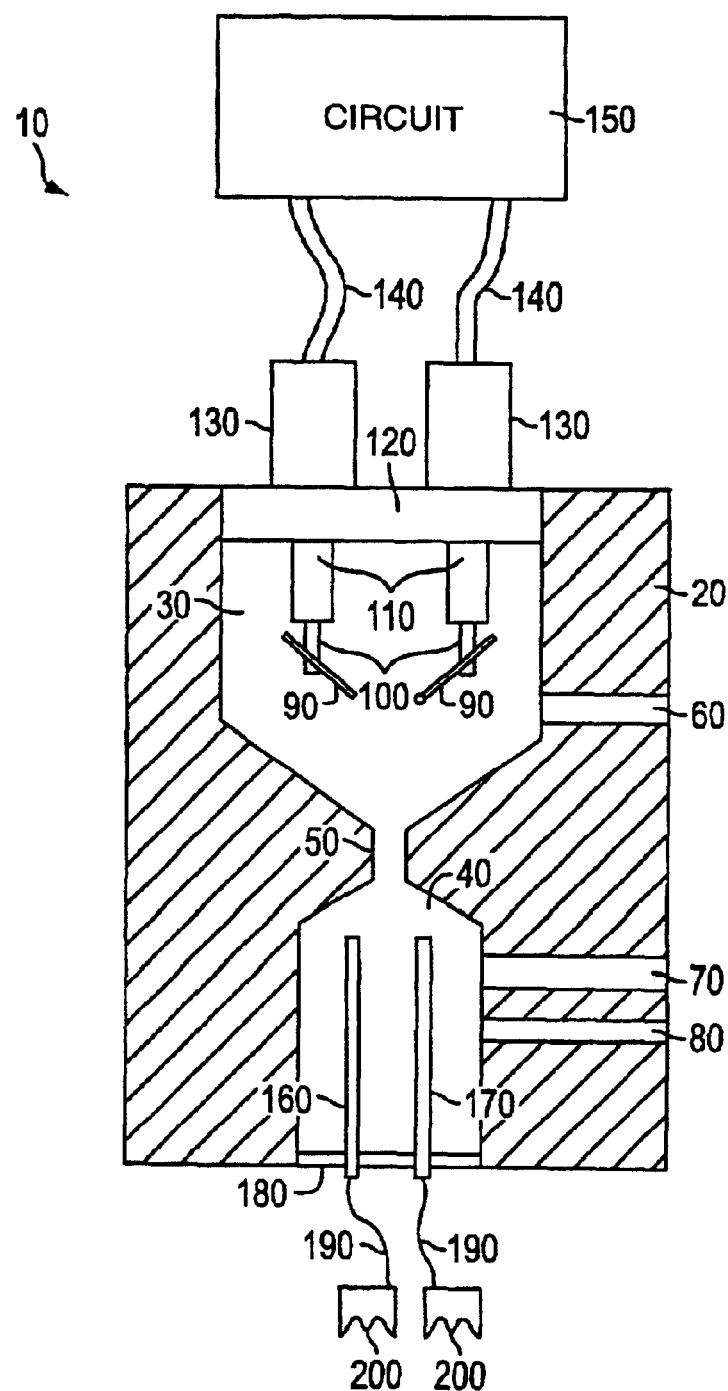
FIG. 1A illustrates a discharge ionization detector according to the related art.
Figure 1B:
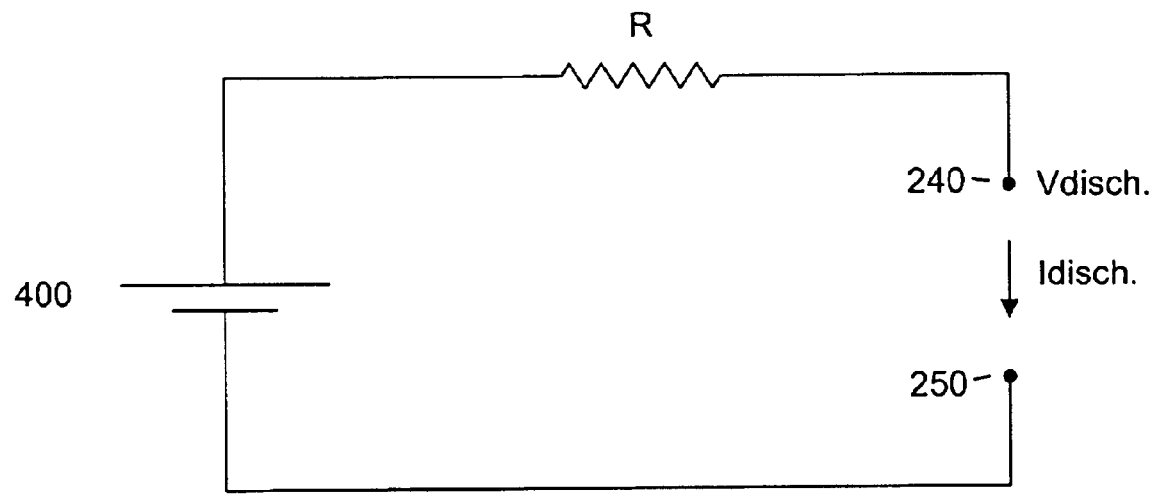
FIG. 1B illustrates an electronic circuit powered by a high-voltage direct current (DC) power supply. This electronic circuit has been used in detectors according to the related art to generate sparks between the spark electrodes of the detector.
Figure 1C:
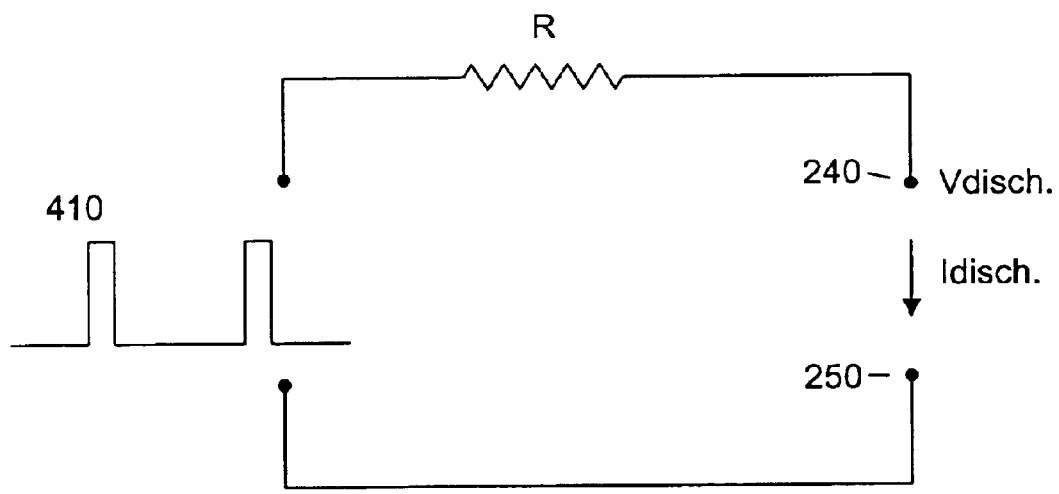
FIG. 1C illustrates an alternate electronic circuit according to the related art wherein high-voltage, short-duration, DC pulses are used to generate sparks between the spark electrodes of a detector.

The circuit 150 illustrated in FIG. 2A does not experience the space charge fluctuations that are associated with circuits 150 powered by DC voltage, sources such as the circuit in FIG. 1B. Also, the circuit illustrated in FIG. 2A does not require the large discharge peak currents seen when using a pulsed DC source, such as the circuit of FIG. 1C.

Figure 3A:
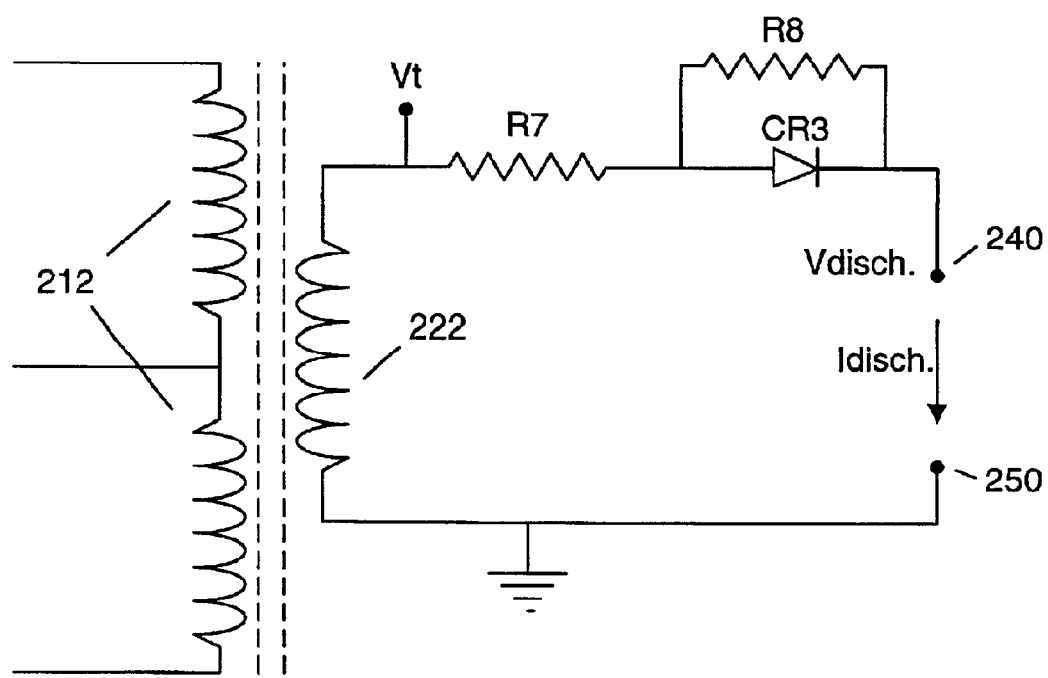
FIG. 3A illustrates another embodiment of an electronic circuit according to the present invention, in which two resistors and a diode are electrically connected to the secondary portion of the transformer.

FIG. 3A illustrates another embodiment of the present invention wherein the electronic circuit 150 includes a transformer 205. The primary portion 210 of the transformer in FIG. 3A can be identical to the primary portion 210 of the transformer 205 illustrated in FIG. 2A. However, the secondary portion 220 of the electronic circuit 150 illustrated in FIG. 3A has a different implementation.

The secondary portion 220 according to the embodiment illustrated in FIG. 3A includes a ground connection, two resistors R7, R8, a high-voltage diode CR3, a first electrode 240 and a second electrode 250. The resistor R8 and the high-voltage diode CR3 are positioned in a parallel configuration and the resistor R7 is electrically connected in series with the parallel configuration. A voltage $V_t$ is monitored between the coils of the secondary portion 220 of the transformer 205 and the resistor R7.

Figure 3B:
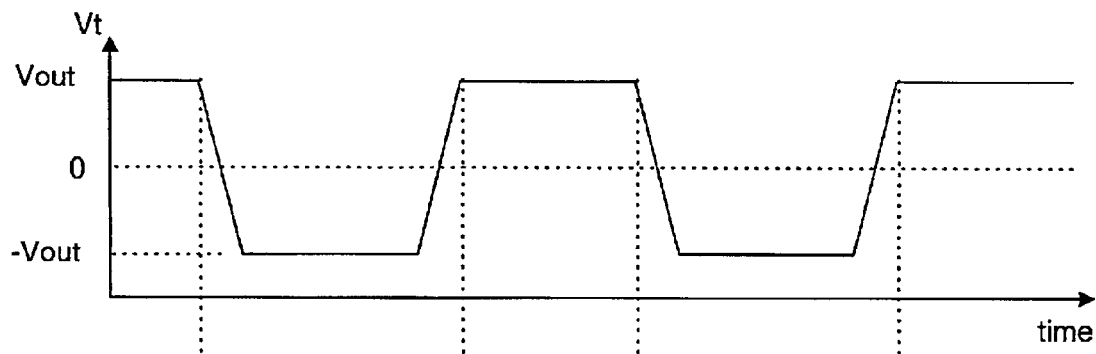
FIGS. 3B–3D illustrate various signals monitored within the electronic circuit illustrated in FIG. 3A.
Figure 3C:
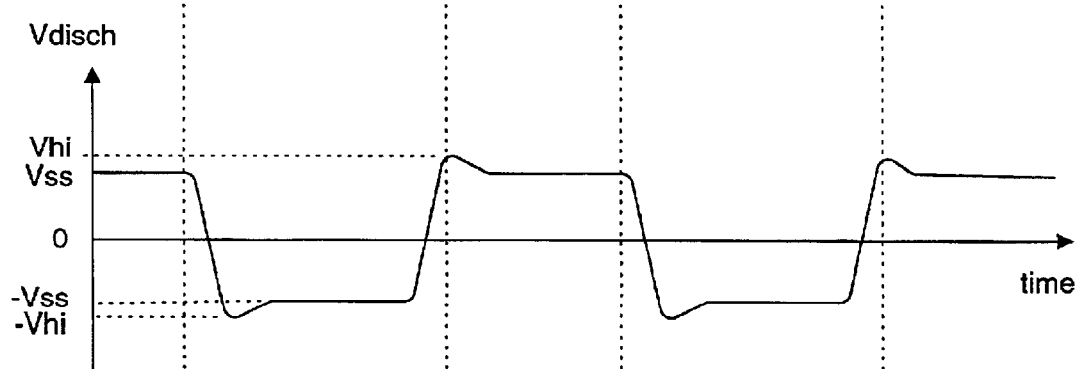
Figure 3D:
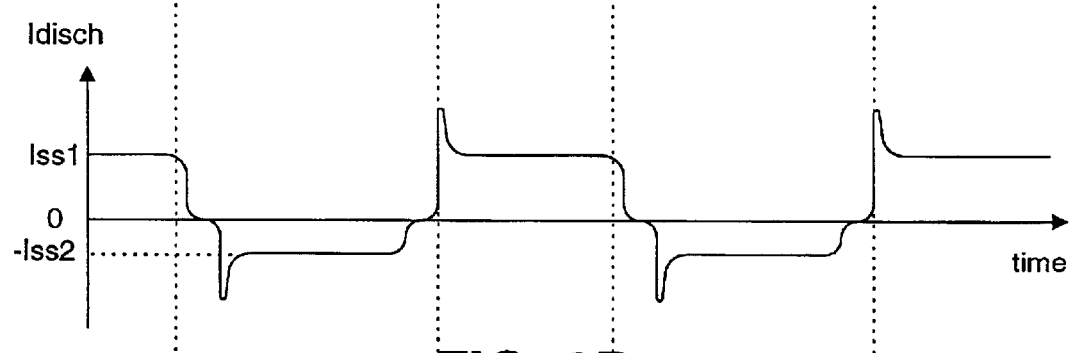

FIGS. 3B–3D illustrate graphs of the wave forms of various signals monitored within the circuit illustrated in FIG. 3A as a function of time. The graph in FIG. 3B illustrates the $V_t$ voltage monitored between the secondary portion 220 coil and resistor R7. As $V_t$ switches between a maximum voltage of $V_{out}$ and a minimum voltage of $-V_{out}$, the switch in value is not instantaneous and a time delay is shown.

The discharge voltage $V_{disch}$ across the first electrode 240 and the second electrode 250 is shown in FIG. 3C. The small difference between the high voltage, $V_{hi}$, seen and the steady state voltage, $V_{ss}$, can, as above, be attributed to ionized gas molecules between pulses.

FIG. 3D shows that the addition of the resistor R8 and the high-voltage diode CR3 in the circuit 150 illustrated in FIG. 3A results in a modulation over time of the current flowing between the first electrode 240 and the second electrode 250. As shown, two steady state current plateaus $I_{ss1}$ and $-I_{ss2}$ exist.

When either the collector electrode 160 or the emitter electrode 170 illustrated in the device in FIG. 1A is the main source of ionization in the ionization chamber 40, the circuit in FIG. 3A is preferred. This preference is due to the fact that the circuit in FIG. 3A saves power while maintaining the same level of ionization. The magnitudes of the two steady state current plateaus $I_{ss1}$, and $-I_{ss2}$ can be determined by the following equations:

$$I_{ss1}=(V_{out}-V_{ss})/R7$$

$$I_{ss2}=(V_{out}-V_{ss})/(R7+R8)$$

Because the first electrode 240 and second electrode 250 illustrated in FIGS. 2A and 3A are electrically connected to the spark electrodes 90 illustrated in FIG. 1A, the transformer-based electronic circuits 150 enhances stability of the electrical discharges across the spark electrodes 90. The circuits illustrated in FIG. 2A and 3A also avoid the large peak currents that allow the use of smaller discharge cross-sectional areas and higher discharge gas linear velocities for linearity enhancement. Further, the embodiments of the present invention discussed above include current monitors 230 that monitor the average current drawn from the discharge input supply and therefore provide additional data concerning the state of the discharge.

The foregoing detailed description has been given for understanding exemplary implementations of the invention only and no unnecessary limitations should be understood therefore as modifications will be obvious to those skilled in the art without departing from the scope of the appended claims and their equivalents.

What is claimed is:

1. An electronic circuit comprising:
   a first electrode for electrical connection to an ionization detector system;
   a second electrode for electrical connection to the ionization detector system;
   a transformer electrically connected to the first electrode and to the second electrode for creating a spark between the first electrode and the second electrode; and
   a conjugated clock input electrically connected to the transformer.

2. The electronic circuit of claim 1, further comprising a first resistor electrically connected to a secondary coil in a secondary portion of the transformer.

3. The electronic circuit of claim 2, further comprising a second resistor electrically connected to the secondary coil in the secondary portion of the transformer.

4. The electronic circuit of claim 3, wherein the second resistor is connected in series with the first resistor.

5. The electronic circuit of claim 3, wherein the second resistor is connected in parallel with a diode.

6. The electronic circuit of claim 1, wherein the transformer comprises:
   a primary portion including a primary coil; and
   a secondary including a secondary coil, wherein the primary coil includes a different number of loops than are present in the secondary coil.

7. The electronic circuit of claim 6, wherein the primary coil includes a greater number of loops than are present in the secondary coil.

8. The electronic circuit of claim 1, further comprising a DC voltage source electrically connected to a primary portion of the transformer.

9. The electronic circuit of claim 8, further comprising a current monitor electrically connected to the DC voltage source.

10. A method of generating an electrical discharge for an ionization detector system comprising:
    providing a first electrode and a second electrode, each electrically connected to the ionization system;
    providing a transformer electrically connected to the first electrode and the second electrode;
    inputting a DC voltage into the primary portion of the transformer; and
    generating a discharge current having at least a first steady-state current plateau and a second steady-state current plateau between the first electrode and the second electrode.

11. The method of claim 10, wherein the providing the transformer step comprises including a first resistor in a secondary portion of the transfer.

12. The method of claim 11, wherein the providing the transformer step comprises including a second resistor in the secondary portion of the transformer.

13. The method of claim 12, wherein the providing the transformer step comprises connecting the second resistor in parallel with a diode.

14. The method of claim 12, further comprising monitoring a current input.

15. The method of claim 12, wherein the providing the transformer step comprises providing a primary coil and a secondary coil in the transformer wherein the primary coil and the secondary coil include a different numbers of loops.

16. The method of claim 15, wherein the providing the transformer step comprises providing the primary coil to have a greater number of loops than the secondary coil.

17. The method of claim 11, wherein the generating the discharge current step comprises generating a substantially constant steady-state current plateau.

18. The method of claim 10, wherein the generating the discharge current step comprises providing the net amplitude of a first steady-state current plateau exceeding the amplitude of a second steady-state current plateau.

19. An electronic circuit comprising:

a first electrode for electrical connection to an ionization detector system;

a second electrode for electrical connection to the ionization detector system;

a transformer electrically connected to the first electrode and to the second electrode for creating a spark between the first electrode and the second electrode;

a DC voltage source electrically connected to a primary portion of the transformer;

a current monitor electrically connected to a primary portion of the transformer; and a resistor, a capacitor and transistor electrically connected in series to the primary portion of the transformer, wherein the capacitor interacts with a current through the resistor to limit a slew rate of a gate voltage on the transistor, which in turn limits a slew rate of the transformer primary voltage.

20. A method of generating an electrical discharge for an ionization detector system comprising:

providing a first electrode and a second electrode, each electrically connected to the ionization system;

providing a transformer electrically that is connected to the first electrode and the second electrode, including a first resistor and a second resistor in a secondary portion of the transformer;

inputting a DC voltage into the primary portion of the transformer;

generating a discharge current between the first electrode and the second electrode; and monitoring a current input; and controlling a slew rate of a voltage in the secondary portion of the transformer for a sufficient amount of time to cause the discharge current to go to zero.

* * * * *